United States Patent
Gramse

(10) Patent No.: US 6,505,073 B2
(45) Date of Patent: Jan. 7, 2003

(54) IMPLANTABLE MEDICAL DEVICE WITH FULL METALLIC CASE

(75) Inventor: Leonard J. Gramse, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 49 days.

(21) Appl. No.: 09/813,203

(22) Filed: Mar. 20, 2001

(65) Prior Publication Data
US 2002/0138114 A1 Sep. 26, 2002

(51) Int. Cl.[7] ............................................... A61N 1/375
(52) U.S. Cl. ........................................................ 607/37
(58) Field of Search ............................... 607/1, 4–5, 9, 607/36–38, 115–116, 119; 439/909

(56) References Cited

U.S. PATENT DOCUMENTS 4,934,366 A * 6/1990 Truex et al. ................... 607/37
6,029,089 A * 2/2000 Hawkins et al. ......... 340/286.01

* cited by examiner

Primary Examiner—Kennedy Schaetzle
Assistant Examiner—Kristen Droesch
(74) Attorney, Agent, or Firm—Thomas J. Nikolai; Nikolai & Mersereau, P.A.

(57) ABSTRACT

An implantable electronic tissue stimulating device for providing therapy to a patient is contained within an full metallic case resulting in reduced size, reduced assembly time, reduced parts cost and reduced labor cost, limits the exposure of the patient to possible allergic reactions to medical adhesives and polyurethanes. A hybrid electronic circuit and a battery for powering same are contained within a first portion of the full metal case and a header assembly including a metal header housing, a connector block holder, its lead connector blocks and a feed-through assembly also form a sealed unit. It is inserted into a second portion of the case with feed-through pins connecting the connector blocks to the hybrid. A weld is employed to join the two halves of the outer case together about its perimeter to form a stimulating device package of a smaller size and reduced manufacturing costs.

11 Claims, 3 Drawing Sheets

IMPLANTABLE MEDICAL DEVICE WITH FULL METALLIC CASE

BACKGROUND OF THE INVENTION

I. Field of the Invention

This invention relates generally to the construction of implantable electronic tissue stimulator systems, and more particularly to a design in which a battery power pulse generator, feed-through assembly and lead header are all contained within a metal case.

II. Discussion of the Prior Art

Implantable electronic tissue stimulating devices, such as cardiac rhythm management devices (pacemakers and defibrillators) and a variety of implantable muscle/nerve stimulators conventionally comprise a battery-powered electronic pulse generator contained within a hermetically sealed metal housing or case and attached to the housing or case is a molded polyurethane lead header. The lead header is commonly affixed to the metal case by metal brackets along with a medical grade adhesive. In this regard, reference is made to the Oleen et al. U.S. Pat. No. 5,261,395, assigned to the assignee of the present application. In that patent, a hybrid electronics board along with a battery power source, is contained within the case and affixed to a generally flat top surface thereof is a header 28 in the form of a molded polyurethane biocompatible body 30. The header has a plurality of lead receiving cavities in which are fitted connector blocks 38 and 46. The connector blocks have aligned bore(s) generally concentric with lead receiving bore(s) formed in the polyurethane header whereby electrical stimulating lead(s) having male terminal pins on the proximal end thereof can be inserted. The connector blocks 36 and 46 are, in turn, connected through the connector pins of a feed-through assembly to points on the electronic circuitry contained within the case 26.

While the arrangement described in the Oleen et al. '395 patent has proven to be highly reliable, it involves a variety of expensive manufacturing processes that necessarily increase the cost of the resulting product. For example, prior to affixing the polyurethane header to the case, it needs to be subjected to a cleaning process, such as plasma cleaning, to remove oil residues leaching out from the polymer to prepare the surface for optimal bond strength. Polyurethane headers may require repeat cleaning if they are not affixed shortly after the cleaning process.

Further, once the polyurethane header is assembled onto the case the adhesive involved is cured and degassed by being subjected to elevated temperatures in an oven for several hours.

Ongoing efforts by the industry to reduce the size of the implantable device have been very successful. Early implantable pacemakers back in the 1960's were about the size of a hockey puck. With advances in microelectronics and integrated circuitry, significantly more features and capabilities have been embodied in implantable devices, such as pacemakers and defibrillators, capable of sizes as small as about 10 cc. Nonetheless, efforts to further reduce the size of implantable pulse generators continue in the industry.

A need, therefore, exists for an implantable electronic tissue stimulating device that is less expensive to manufacture and whose physical size can be reduced compared to state-of-the-art commercial designs.

SUMMARY OF THE INVENTION

The foregoing needs are met in accordance with the invention by providing an implantable tissue stimulating device in which a battery and an electronic circuit powered by the battery, the header assembly, including its connector blocks and feed-through assembly, are all contained within an all-metal case. This result is achieved by providing a metal header housing having a cavity for containing a connector block holder that is formed from an insulating material and which contains at least one electrically conductive lead connector. The connector block holder and lead connector are insertable into the cavity of the header housing through an aperture that leads to the cavity in the header housing. A feed-through assembly, comprising a metal feed-through mounting plate that supports, but is insulated from, at least two conductive pins, is welded into the aperture to thereby hermetically seal the metal header housing from the electronic circuit and battery compartment. One of the two conductive pins connects to a first point on the electronic circuit and to the at least one lead connector while another of the conductive pins connects a second point on the electronic circuit to the metal header housing.

Following this construction, in which all components are contained within a single metal case, the need for medical adhesive and the problems associated with it are obviated. Furthermore, by eliminating a molded polyurethane header, manufacturing cost reductions are realized. The full metal case, where the metal in question is titanium, allows further size reductions and simplifies the creation of a hermetically sealed environment for the electronic circuit and battery. Patients who may have an allergic reaction to medical grade adhesives and/or the polyurethane used for the header material also benefit from the use of a full metal (titanium) case.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
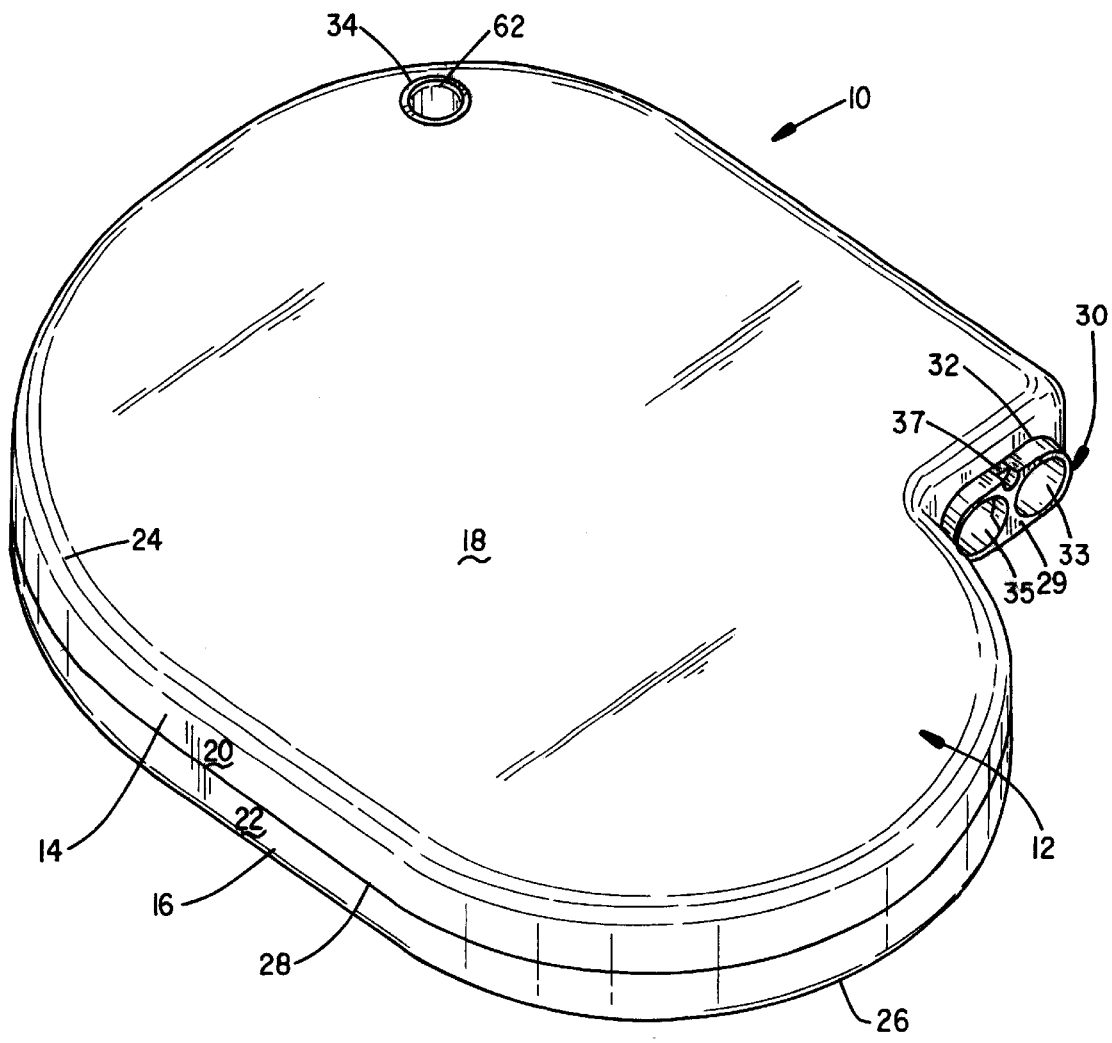
FIG. 1 is a perspective view of the implantable medical tissue stimulating device constructed in accordance with the present invention.

Referring to FIG. 1, there is shown a perspective view of an implantable medical tissue stimulating device constructed in accordance with the present invention. The device is indicated generally by numeral 10 and includes a case or housing 12 comprising an upper half 14 and a lower half 16. The housing or case halves are preferably formed from a body compatible metal, with titanium being preferred. Each of the case halves is of a predetermined shape and, without limitation, may have the "bootie" shape depicted in FIG. 1 and a thickness of about 10 mils. Each of the case halves 14 and 16 has a generally flat major surface, as at 18 on the upper case half, with a peripheral wall 20 and 22 extending generally perpendicular to the major surface. A curved contour 24 and 26 is provided along the edge where the peripheral walls 20 and 22 intersect with their respective major surfaces 18.

When the case halves 14 and 16 are juxtaposed as illustrated in FIG. 1, the peripheral walls 20 and 22 meet along a line 28 and a welding technique is used to join the mating edges so as to define a hollow chamber within the assembly.

With continued reference to FIG. 1, an oval collar portion 29 of a header housing 30, yet to be described, extends out through an opening 32 in the mating case halves 14 and 16. A hermetic seal is provided between the header housing collar portion 29 and the case 12 by welding the seam between the case and the projecting collar portion of the header housing along the line defined by the opening 32. The collar portion 29 of the header housing 30 is shown as having two longitudinal bores 33 and 35 that are adapted to receive therein proximal connector terminals of a tissue stimulating lead. A slot 37 is formed in the oval collar portion 29 that extends transversely to the axes of the bores 33 and 35 so as to intersect those bores at locations offset from the centerline of the bores. The slot 37 is adapted to receive a wedging insert 39 (FIG. 2) so as to act as a lead retaining clip in a fashion described in the Frey et al. U.S. Pat. No. 4,860,750, the teachings are which are hereby incorporated by reference.

Also visible in the view of FIG. 1 is a suture hole 34 that extends transversely through the case 12 and the underlying header housing member 30 (FIG. 2) and again the seam between the header housing and the case is welded to create a hermetic seal.

Figure 2:
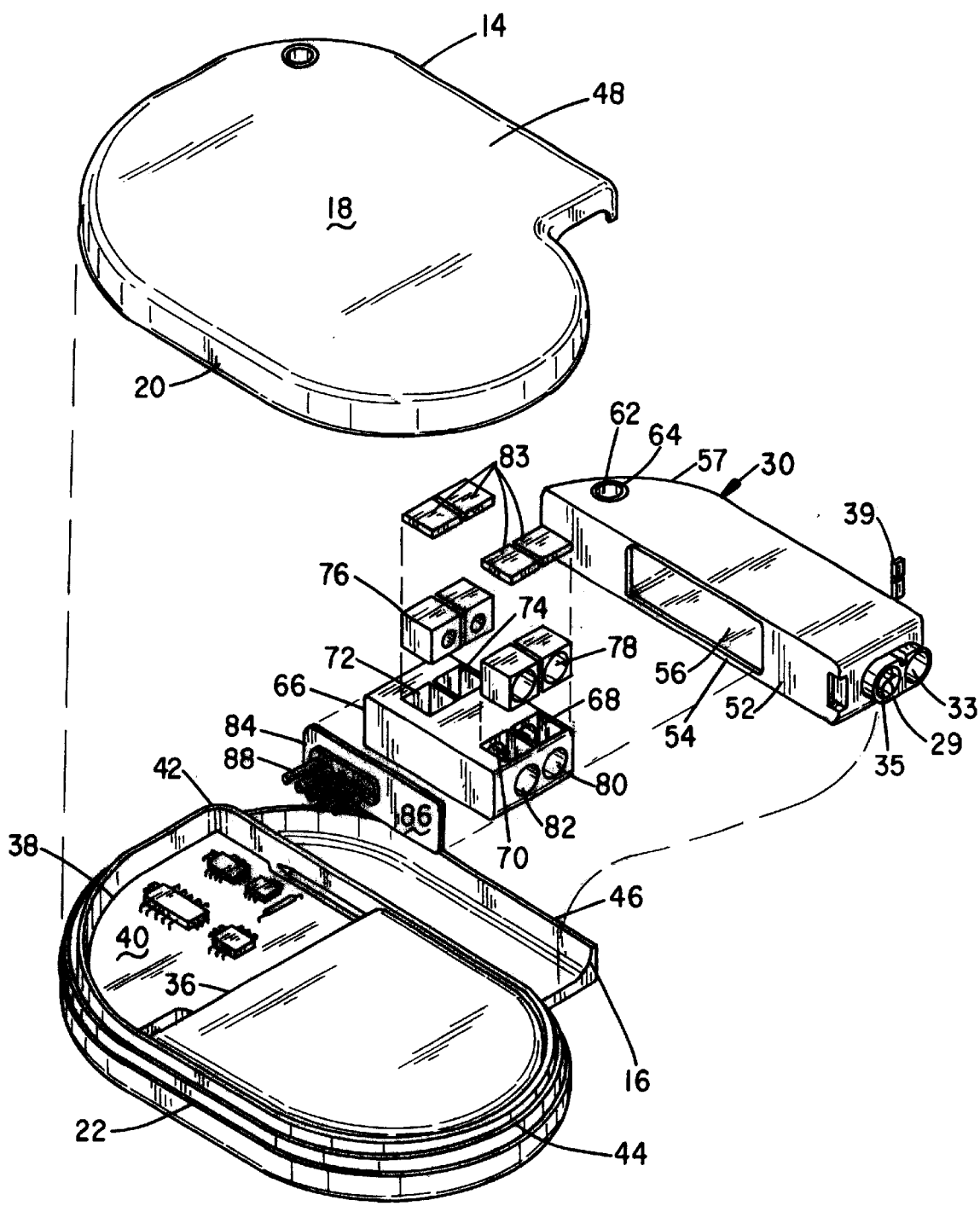
FIG. 2 is a greatly enlarged exploded view of an implantable medical tissue stimulating device.

Referring next to the exploded view of FIG. 2, there is shown disposed within the confines of the lower case half 22 a battery 36 and a hybrid circuit 38. Hybrid circuit 38 may comprise of a substrate 40 having a pattern of printed circuitry formed thereon (not shown) that interconnects electronic circuit components which may comprise both analog and digital devices.

Also shown contained within the lower case half 22 is a telemetry coil 42 that surrounds the battery 36 and hybrid circuit 38 so as to reside in close proximity to the mating side walls 20 and 22 of the case when the two are joined together. Disposed between the telemetry coil 42 and the sidewalls 20–22 is a weld ring 44 that functions to protect the circuit and battery from damage due to heating as the weld is being formed along the seam line 28 (FIG. 1). The weld ring 44 is preferably made of titanium and functions as a heat sink to absorb and reflect heat away from the weld site, therefore, protecting the circuitry.

The case halves 20 and 22 include segments 46 and 48 designed and dimensioned to contain the metal header housing 30 therebetween. The header housing 30 is also preferably fabricated from a block of titanium and is machined so as to have a flat surface 52 with a generally rectangular opening 54 leading to a cavity 56 and a radiused edge 57 conforming to the shape of the case halves. As indicated above, lead receiving bore(s) 33 and 35 extend longitudinally through the header housing 30 to intersect the cavity 56. Extending transversely through the thickness dimension of the header housing 30 is a suture hole 62 which is surrounded by a raised collar 64 on both sides of the header housing. The height of the raised collar is approximately the thickness of the case halves 14 and 16 so that when the weld is formed about suture hole 34 (FIG. 1), the circular peripheral edge of the collar is flush with the top surface 18 of the case.

The cavity 56 is dimensioned to receive a connector block holder member 66 therein. The connector block holder is preferably formed from a suitable plastic, such as polyurethane, and includes rectangular sockets 68, 70, 72 and 74 that are dimensioned to receive four spring contact connector blocks, as at 76, therein. The individual ones of the four connector blocks are separated from one another by the insulating material comprising the intermediate walls between connector block sockets 68–70 and 72–74.

Figure 3:
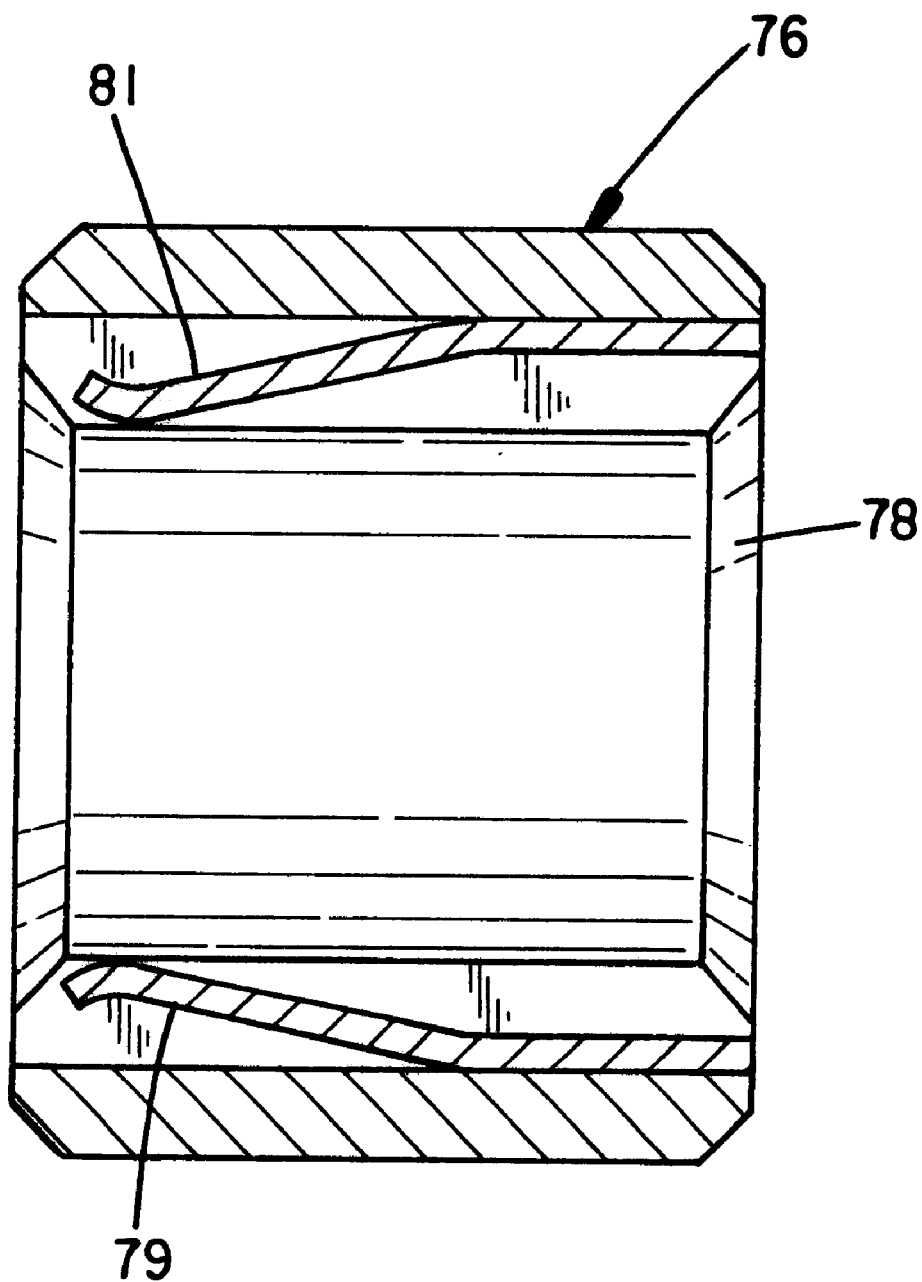
FIG. 3 is a cross-sectional view of a spring contact connector block shown in the exploded view of FIG. 2.

As shown in the cross-sectioned view of FIG. 3, each of the spring contact connector blocks 76 includes a longitudinally extending bore, as at 78, with the longitudinal bore(s) being disposed concentrically with openings 80 and 82 formed in the connector block holder 66. Metal spring elements, 79 and 81 are welded to the wall of the bore 78 and include inwardly extending contact segments adapted to engage the connector pin of the lead terminal. When the connector block holder 66, with the spring contact connector blocks 76 placed in their respective rectangular sockets, is inserted within the cavity 56, the openings 80 and 82 as well as the bore(s) 78 are in alignment with the lead receiving bores 33 and 35 in the titanium header housing 30. Insulating layers 83 are placed between the spring contact connector blocks 76 and the header housing 30 to prevent short circuiting of the connector blocks to one another.

Before the header housing 30 is placed between the segments 46 and 48 of the case halves 20 and 22 prior to these two case halves being welded together, a feed-through assembly 84 is welded so as to cover the opening 54 in the header housing 30. The feed-through assembly 84 comprises a metal plate 86 that supports a plurality of conductive feed-through pins, as at 88, that remain insulated from the metal plate 86 by ceramic bushings (not shown). The feed-through assembly may be similar in construction to what is shown in U.S. Pat. No. 5,905,627 to Brendel et al. such that EMI filter capacitors exist between the individual conductive pins and a ground pin. The teachings of the aforementioned Brendel et al. '627 patent are hereby incorporated by reference.

In making electrical connections, the feed-through pins are individually connected to one of the spring contact connector blocks 76, with a further one of the plurality of feed-through pins being welded or otherwise directly affixed to the material comprising the metal header housing 30. More particularly, conductive (platinum) wires from the feed-through assembly are routed through channels formed in the polyurethane connector block holder and are welded to the spring contact connector blocks 76. Once the feed-through pin support plate 86 is welded to the header housing 30 and the header housing is sealed within the case halves 14 and 16, the chamber containing the battery 36 and the hybrid circuit 38 are hermetically sealed and shielded from exposure to electromagnetic interference (EMI). Only the components within the header housing 30 are exposed to the atmosphere through lead entry bores 33 and 35. However, when the medical device is to be implanted, the proximal ends of the stimulating lead(s) used with the stimulating device are provided with elastomeric seal rings that cooperate with the walls defining the lead entry bores 33 and 35 to create a seal, preventing body fluids from entering the cavity 56 of the header housing 30 after implant. As mentioned, the lead terminals may be locked within the lead-receiving bores 33 and 35 of the header housing 30 by inserting locking wedge 39 in slot 37 formed in the protruding collar portion 29 of the header housing 30.

Summarizing the assembly, feed-through pins 88 are routed through channels and spot-welded to the spring-contact connector blocks 76 within the connector block holder 66. Insulators 83 are placed over the connector blocks to isolate them from the titanium header housing 30. The feed-through support plate or flange 86 is -welded to the titanium header housing 30, providing EMI isolation and a hermetic seal from the header housing to the compartment of the case containing the battery 36 and the hybrid circuit 38. The header assembly is then inserted into the bottom case half 16 and the feed-through pins are spot-welded to connection points on the hybrid circuit 38. The top case half 14 is assembled to the bottom case half 16 and a weld operation is performed around the perimeter, lead entry area and suture hole on both the top and bottom case sides.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable tissue stimulating device comprising:
   (a) a battery;
   (b) an electronic circuit powered by said battery;
   (c) a hermetically sealed, body compatible metal case for containing said battery and said electronic circuit;
   (d) a connector block holder formed from an insulating material and containing at least one electrically conductive lead connector;
   (e) a metal header housing having a cavity and an aperture leading to said cavity, said connector block holder and lead connector being insertable into the cavity of the header housing through said aperture;
   (f) a feed-through assembly comprising a metal feed through mounting plate with at least two conductive pins supported by but insulated from the mounting plate, said mounting plate hermetically sealing said aperture, one of the pins connecting the first node on said electronic circuit to said lead connector and another of said pins connecting the second node on said electronic circuit to the metal header housing and wherein said metal header housing is disposed within the metal case along with the battery and electronic circuit.

2. The implantable tissue stimulating device of claim 1 wherein the metal case comprises first and second metal case halves, each half including a generally flat major surface of a predetermined shape configuration and a peripheral side wall extending perpendicularly to the major surface, said case halves being welded together along a line of contact of the peripheral side walls when the first and second halves are juxtaposed to define a hermetically sealed chamber for containing the battery, the electronic circuit and the header housing.

3. The implantable tissue stimulating device of claim 2 and further including a telemetry coil contained in the sealed chamber adjacent the peripheral side wall and in surrounding relation to the battery and electronic circuit.

4. The implantable tissue stimulating device of claim 1 and further including a filter capacitor connected between the at least two conductive pins.

5. The implantable tissue stimulating device of claim 1 wherein the metal header housing includes a lead terminal receiving opening that is in alignment with an opening in the connector block holder leading to the lead connector.

6. The implantable tissue stimulating device of claim 2 wherein the metal header housing is in conductive contact with the metal case.

7. The implantable tissue stimulating device of any one of claims 1–6 wherein the metal case is made from titanium.

8. The implantable tissue stimulating device of claim 1 wherein the electrically conductive lead connector comprises:
   (a) a block of a conductive material having a longitudinal bore formed therethrough; and
   (b) first and second arcuate spring members of a conductive material, each having a first portion conforming to a wall of the bore and being welded thereto and a second portion inwardly tapered toward a centerline of the bore.

9. The implantable tissue stimulating device of claim 1 wherein the electrically conductive lead connector is electrically insulated from the metal header housing.

10. The implantable tissue stimulating device of claim 8 wherein the electrically conductive lead connector is electrically insulated from the metal header housing.

11. The implantable tissue stimulating device of claim 5 wherein the header housing includes a slot extending transversely to the lead terminal receiving opening, the slot being offset from a central axis of the opening yet intersecting said opening and a wedge member adapted to be inserted into the slot for forcing a terminal portion of a lead inserted through the opening tightly against a surface of the header housing defining the opening.

* * * * *